(12) United States Patent
Park

(10) Patent No.: US 11,813,112 B2
(45) Date of Patent: Nov. 14, 2023

(54) ULTRASOUND DIAGNOSIS APPARATUS AND METHOD OF DISPLAYING ULTRASOUND IMAGE

(71) Applicant: SAMSUNG MEDISON CO., LTD., Hongcheon-gun (KR)

(72) Inventor: Jin-ki Park, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 407 days.

(21) Appl. No.: 16/114,459

(22) Filed: Aug. 28, 2018

(65) Prior Publication Data

US 2019/0247015 A1    Aug. 15, 2019

(30) Foreign Application Priority Data

Feb. 9, 2018  (KR) ........................ 10-2018-0016566

(51) Int. Cl.
*A61B 8/00* (2006.01)
*A61B 8/08* (2006.01)
(Continued)

(52) U.S. Cl.
CPC ............ *A61B 8/0866* (2013.01); *A61B 8/085* (2013.01); *A61B 8/461* (2013.01); *A61B 8/469* (2013.01);
(Continued)

(58) Field of Classification Search
CPC ......... A61B 8/463; A61B 8/0866; A61B 8/00; A61B 8/54; A61B 8/14; A61B 8/5207;
(Continued)

(56) References Cited

U.S. PATENT DOCUMENTS 8,204,576 B2    6/2012  Ikuma et al.
8,355,553 B2    1/2013  Fidrich et al.
(Continued)

FOREIGN PATENT DOCUMENTS

EP    2783635 A1    10/2014
JP    2008-154833 A    7/2008
(Continued)

OTHER PUBLICATIONS

Achiron R, Gindes L, Zalel Y, Lipitz S, Weisz B. Three- and four-dimensional ultrasound: new methods for evaluating fetal thoracic anomalies. Ultrasound Obstet Gynecol. Jul. 2008;32(1):36-43. doi: 10.1002/uog.5308. PMID: 18548479.*

(Continued)

*Primary Examiner* — Joel Lamprecht
(74) *Attorney, Agent, or Firm* — Sughrue Mion, PLLC

(57) ABSTRACT

Provided are an ultrasound diagnosis apparatus and a method of displaying an ultrasound image. The ultrasound diagnosis apparatus includes: one or more processors configured to acquire ultrasound image data with respect to a fetus and generate an ultrasound image based on the ultrasound image data; a display configured to display the ultrasound image; and an input interface configured to receive position type information, wherein the one or more processors are further configured to determine positions of organs in the ultrasound image based on the position type information and control the display to display information about the organs together with the ultrasound image, based on the determined positions.

12 Claims, 19 Drawing Sheets

(51) Int. Cl.
*G06T 7/00* (2017.01)
*G06T 7/62* (2017.01)

(52) U.S. Cl.
CPC .......... *A61B 8/5223* (2013.01); *A61B 8/5292* (2013.01); *A61B 8/54* (2013.01); *G06T 7/0012* (2013.01); *G06T 7/62* (2017.01); *A61B 8/483* (2013.01); *A61B 8/5207* (2013.01); *G06T 2207/10132* (2013.01); *G06T 2207/30044* (2013.01)

(58) Field of Classification Search
CPC ..... A61B 8/5223; A61B 8/467; A61B 8/4427; A61B 8/468; A61B 8/469; A61B 8/5292; G06T 7/0012; G06T 15/08
See application file for complete search history.

(56) References Cited

U.S. PATENT DOCUMENTS

| | | | | |
|---|---|---|---|---|
| 8,882,671 | B2 | 11/2014 | Sasaki et al. | |
| 2009/0105597 | A1* | 4/2009 | Abraham | A61B 8/08 600/466 |
| 2010/0099987 | A1 | 4/2010 | Sasaki et al. | |
| 2013/0072797 | A1* | 3/2013 | Lee | G01S 15/8993 600/443 |
| 2014/0282142 | A1* | 9/2014 | Lin | A61B 8/461 715/765 |
| 2014/0296711 | A1* | 10/2014 | Lee | A61B 8/14 600/443 |
| 2015/0094584 | A1* | 4/2015 | Abe | A61B 8/483 600/443 |
| 2015/0190112 | A1 | 7/2015 | Yeo et al. | |
| 2016/0361043 | A1 | 12/2016 | Kim et al. | |
| 2017/0206659 | A1 | 7/2017 | Perrey et al. | |
| 2017/0360415 | A1* | 12/2017 | Rothberg | A61B 8/12 |
| 2018/0350064 | A1* | 12/2018 | Man | A61B 8/5246 |

FOREIGN PATENT DOCUMENTS

| | | |
|---|---|---|
| JP | 2010-115483 A | 5/2010 |
| JP | 2012-100815 A | 5/2012 |
| KR | 10-2014-0118058 A | 10/2014 |
| KR | 10-1595718 B1 | 2/2016 |
| WO | 2009/136461 A1 | 11/2009 |

OTHER PUBLICATIONS

Rajiah P, Mak C, Dubinksy TJ, Dighe M. Ultrasound of fetal cardiac anomalies. AJR Am J Roentgenol. Oct. 2011;197(4):W747-60. doi: 10.2214/AJR.10.7287. PMID: 21940548.*
Communication dated Mar. 29, 2019, issued by the European Patent Office in counterpart European Application No. 18189382.7.
Communication dated Aug. 28, 2023 from the Korean Intellectual Property Office in KR Application No. 10-2018-0016566.

* cited by examiner

Cardiac Position

Levocardia

Mesocardia

Dextrocardia

ULTRASOUND DIAGNOSIS APPARATUS AND METHOD OF DISPLAYING ULTRASOUND IMAGE

CROSS-REFERENCE TO RELATED APPLICATION(S)

This application is based on and claims priority under 35 U.S.C. § 119 to Korean Patent Application No. 10-2018-0016566, filed on Feb. 9, 2018, in the Korean Intellectual Property Office, the disclosure of which is incorporated by reference herein in its entirety.

BACKGROUND

1. Field

The disclosure relates to ultrasound imaging apparatuses and methods of displaying an ultrasound image, and more particularly, to ultrasound diagnosis apparatuses and methods for obtaining an ultrasound image of a fetus by using ultrasound waves and outputting organ information of the fetus together with the obtained ultrasound image.

2. Description of Related Art

Ultrasound diagnosis apparatuses transmit ultrasound signals generated by transducers of a probe to an object and receive information of signals reflected from the object, thereby obtaining at least one image of an internal part (e.g., soft tissues or blood flow) of the object. In particular, ultrasound diagnosis apparatuses are used for medical purposes including observing an internal area of an object, detecting foreign substances, and assessing injuries. Such ultrasound diagnosis apparatuses exhibit high stability, display images in real-time, and are safe due to lack of radiation exposure, compared to diagnostic X-ray apparatuses. Therefore, ultrasound diagnosis apparatuses have been widely used together with other types of imaging diagnosis apparatuses including a computed tomography (CT) apparatus and a magnetic resonance imaging (MRI) apparatus.

SUMMARY

Provided are methods and apparatuses for providing a more precise ultrasound image of a fetus, and more particularly, methods and apparatuses whereby the presence of morphologic abnormalities in a fetus may be easily determined by outputting organ information of a fetus together with an ultrasound image of the fetus.

Additional aspects will be set forth in part in the description which follows and, in part, will be apparent from the description, or may be learned by practice of the presented embodiments.

In accordance with an aspect of the disclosure, an ultrasound diagnosis apparatus includes: one or more processors configured to acquire ultrasound image data with respect to a fetus and generate an ultrasound image based on the ultrasound image data; a display configured to display the ultrasound image; and an input interface configured to receive position type information, wherein the one or more processors are further configured to determine positions of organs in the ultrasound image based on the position type information and control the display to display information about the organs together with the ultrasound image, based on the determined positions.

The position type information may include position information of a heart and position information of an abdomen.

The input interface may be further configured to receive one position among levocardia, mesocardia, dextrocardia, and ectopiacordis as the position information of the heart.

The input interface may be further configured to receive one position of situs solitus and heterotaxia as the position information of the abdomen.

The one or more processors may be further configured to select one of predesignated types of positions as the received position type information, based on the position information of the heart and the position information of the abdomen.

The one or more processors may be further configured to control, based on the determined positions, the display to display one of a name and an orientation of each of the organs at their corresponding determined positions, together with the ultrasound image.

The organs may include lungs, a liver, and a spleen.

The one or more processors may be further configured to determine left and right sides of the fetus, based on the determined positions and the received position type information and control the display to display information about the determined left and right sides of the fetus together with the ultrasound image.

The one or more processors may be further configured to control the display to display, together with the ultrasound image, the information about the left and right sides of the fetus in a form of an arrow.

The one or more processors may be further configured to control the display to display the position type information together with the ultrasound image.

In accordance with another aspect of the disclosure, a method of displaying an ultrasound image includes: acquiring ultrasound image data with respect to a fetus; generating an ultrasound image based on the ultrasound image data and displaying the ultrasound image; receiving position type information; determining positions of organs in the ultrasound image, based on the position type information; and displaying information about the organs together with the ultrasound image, based on the determined positions.

The position type information may include information about a type of cardiac position and information about a type of abdominal organ position.

The receiving of the position type information may include receiving the cardiac position.

The receiving of the cardiac position may include receiving one position among levocardia, mesocardia, dextrocardia, and ectopiacordis.

The receiving of the position type information may further include receiving the abdominal organ position and selecting one of predesignated types of positions as the received position type information, based on the cardiac position and the abdominal organ position.

The position type information may include one of situs solitus and situs abnormality.

The displaying of the information about the organs together with the ultrasound image based on the determined positions may include displaying a name or an orientation of each of the organs at their corresponding determined positions, together with the ultrasound image.

The method may further include determining left and right sides of the fetus, based on the determined positions and the received position type information, and displaying information about the determined left and right sides of the fetus together with the ultrasound image.

The displaying of the information about the determined left and right sides of the fetus may include displaying, together with the ultrasound image, the information about the determined left and right sides of the fetus as a text.

In accordance with another aspect of the disclosure, a non-transitory computer-readable recording medium has recorded thereon a computer program code which, when read and executed by a processor, performs a method of displaying an ultrasound image. The method includes: acquiring ultrasound image data with respect to a fetus; generating an ultrasound image based on the ultrasound image data and displaying the ultrasound image; receiving position type information; determining positions of organs in the ultrasound image, based on the position type information; and displaying information about the organs together with the ultrasound image, based on the determined positions.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
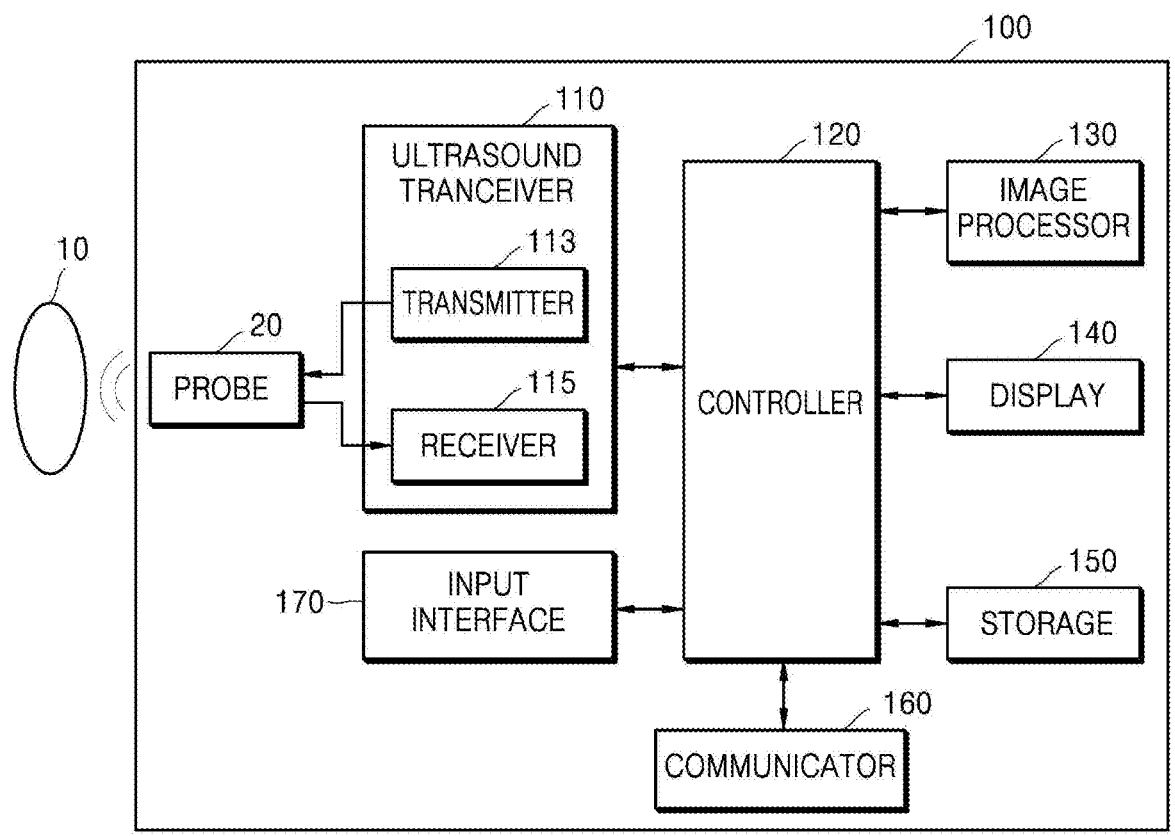
FIG. 1 is a block diagram illustrating an ultrasound diagnosis apparatus according to an embodiment.

The present specification describes principles of the present disclosure and sets forth embodiments thereof to clarify the scope of the present disclosure and to allow those of ordinary skill in the art to implement the embodiments. The present embodiments may have different forms and should not be construed as being limited to the descriptions set forth herein.

Like reference numerals refer to like elements throughout. The present specification does not describe all components in the embodiments, and common knowledge in the art or the same descriptions of the embodiments will be omitted below. Terms such as "part" and "portion" used herein may be implemented using hardware or software, and according to embodiments, a plurality of "parts" or "portions" may be formed as a single unit or element, or a single "part" or "portion" may include a plurality of units or elements. Expressions such as "at least one of," when preceding a list of elements, modify the entire list of elements and do not modify the individual elements of the list. Hereinafter, the operating principles and embodiments of the disclosure will be described in detail with reference to the accompanying drawings.

In embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

FIG. 1 is a block diagram illustrating a configuration of an ultrasound diagnosis apparatus 100, i.e., a diagnostic apparatus, according to an embodiment.

Referring to FIG. 1, the ultrasound diagnosis apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound diagnosis apparatus 100 may be of a cart-type or a portable-type ultrasound diagnosis apparatus which is portable, movable, mobile, or hand-held. Examples of the portable-type ultrasound diagnosis apparatus may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound diagnosis apparatus 100 may be formed in one body (e.g., disposed in a single housing), or the probe 20 and the ultrasound diagnosis apparatus 100 may be formed separately (e.g., disposed separately in separate housings) but linked wirelessly or via wires. In addition, the ultrasound diagnosis apparatus 100 may include one or more probes 20 according to embodiments.

The controller 120 may control the transmitter 113 for the transmitter 113 to generate transmitting signals to be applied to each of the plurality of transducers based on a position and a focal point of the plurality of transducers included in the probe 20.

The controller 120 may control the ultrasound receiver 115 to generate ultrasound data by converting reception signals received from the probe 20 from analogue to digital signals and summing the reception signals converted into digital form, based on a position and a focal point of the plurality of transducers.

The image processor 130 may generate an ultrasound image by using ultrasound data generated from the ultrasound receiver 115.

The display 140 may display a generated ultrasound image and various pieces of information processed by the ultrasound diagnosis apparatus 100. The ultrasound diagnosis apparatus 100 may include two or more displays 140 according to the present embodiment. The display 140 may include a touch screen in combination with a touch panel.

The controller 120 may control the operations of the ultrasound diagnosis apparatus 100 and flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data. For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include command languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an embodiment is not limited thereto.

An example of the ultrasound diagnosis apparatus 100 according to the present embodiment is described below with reference to FIGS. 2A, 2B, and 2C.

Figure 2C:
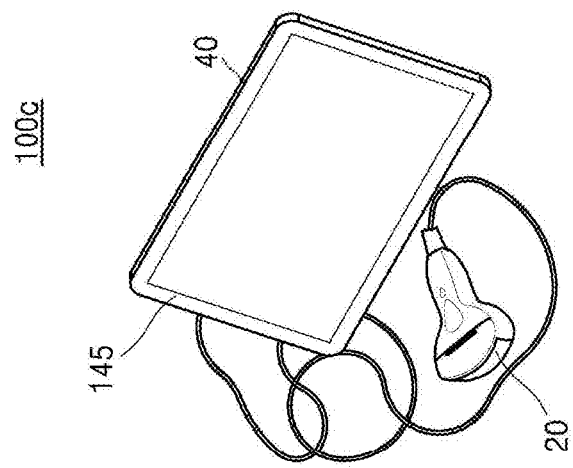
FIGS. 2A, 2B, and 2C are diagrams respectively illustrating ultrasound diagnosis apparatuses according to an embodiment.
Figure 2B:
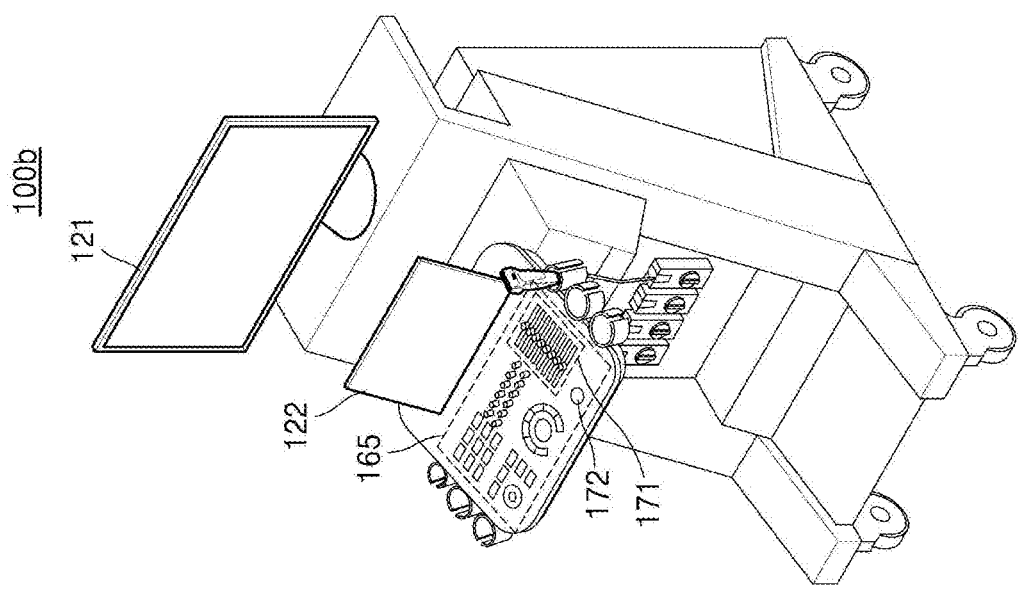
Figure 2A:
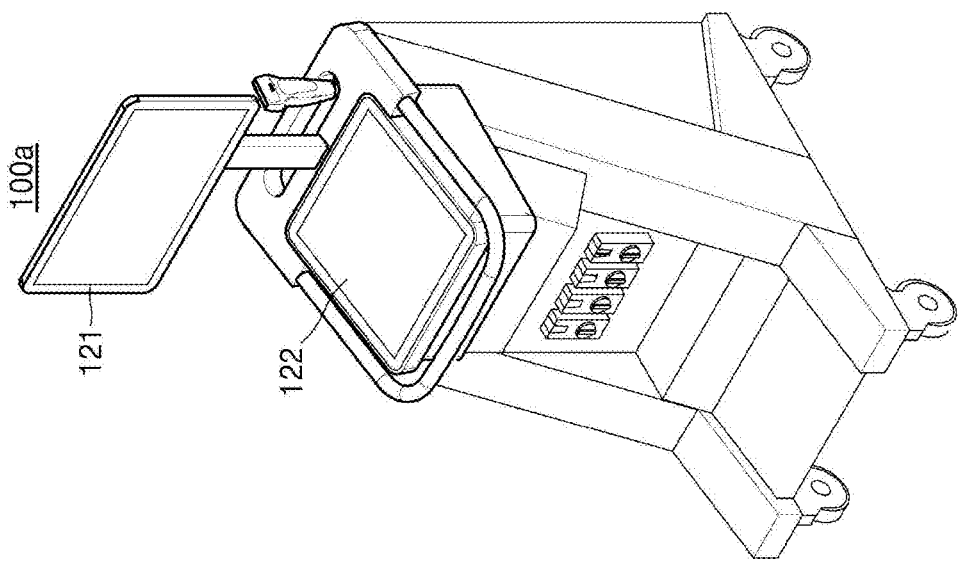

FIGS. 2A, 2B, and 2C are diagrams illustrating ultrasound diagnosis apparatuses according to an embodiment.

Referring to FIGS. 2A and 2B, the ultrasound diagnosis apparatus 100a or 100b may include a main display 121 and a sub-display 122. At least one among the main display 121 and the sub-display 122 may include a touch screen. The main display 121 and the sub-display 122 may display ultrasound images and/or various information processed by the ultrasound diagnosis apparatus 100a or 100b. The main display 121 and the sub-display 122 may provide graphical user interfaces (GUI), thereby receiving user's inputs of data to control the ultrasound diagnosis apparatus 100a or 100b. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus 100a or 100b may control the display of the ultrasound image on the main display 121 by using the input control data.

Referring to FIG. 2B, the ultrasound diagnosis apparatus 100b may include a control panel 165. The control panel 165 may include buttons, trackballs, jog switches, or knobs, and may receive data to control the ultrasound diagnosis apparatus 100b from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100b may keep displaying a frame image at that time point.

The buttons, trackballs, jog switches, and knobs included in the control panel 165 may be provided as a GUI to the main display 121 or the sub-display 122.

Referring to FIG. 2C, the ultrasound diagnosis apparatus 100c may be implemented as a portable ultrasound diagnosis apparatus. An example of the portable ultrasound diagnosis apparatus may include, for example, smart phones including probes and applications, laptop computers, personal digital assistants (PDAs), or tablet PCs, but an embodiment is not limited thereto.

The ultrasound diagnosis apparatus 100c may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100, and a GUI.

Figure 3:
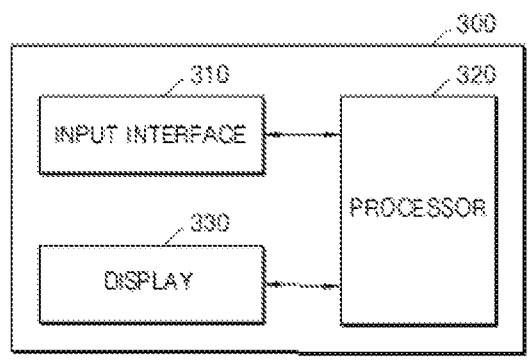
FIG. 3 is a block diagram of a configuration of an ultrasound diagnosis apparatus according to an embodiment.

FIG. 3 is a block diagram of a configuration of an ultrasound diagnosis apparatus 300 according to an embodiment.

Referring to FIG. 3, the ultrasound diagnosis apparatus 300 according to the present embodiment includes an input interface 310, a processor 320, and a display 330. According to an embodiment, the ultrasound diagnosis apparatus 300 may include fewer components or further include other components than those shown in FIG. 3. For example, instead of including the input interface 310, the ultrasound diagnosis apparatus 300 may receive a user input from a separate device.

According to an embodiment, the processor 320 may acquire ultrasound data with respect to an object. The object may be a living body including a fetus. In an embodiment, the fetus refers to an individual from an early stage of pregnancy to the moment of birth of an animal such as a mammal.

A method whereby the processor 320 acquires ultrasound data with respect to an object may be implemented in various ways according to embodiments. For example, the ultrasound diagnosis apparatus 300 may transmit ultrasound waves to an object and detect echo signals via the ultrasound transceiver 110 and the probe 20 described with reference to FIG. 1.

The processor 320 may generate an ultrasound image based on the acquired ultrasound data. The ultrasound image generated by the processor 320 may take different forms. For example, the ultrasound image may include at least one of an amplitude (A) mode image, a brightness (B) mode image, and a motion (M) mode image. According to an embodiment, the processor 320 may process echo signals to produce volume data and perform volume rendering on the volume data to thereby generate a 3D ultrasound image. Furthermore, the processor 320 may generate an elasticity image by imaging deformation of the object due to pressure and produce an ultrasound image such that various pieces of additional information may be represented therein by using text and graphics.

The processor 320 may also control the display 330 to display the generated ultrasound image. The display 330 may be provided as various forms of displays including a liquid crystal display (LCD) and display information processed by the processor 320. According to an embodiment, the processor 320 may control the display 330 to further display an interface for selecting position type information on the display 330.

When an object to be measured by the ultrasound diagnosis apparatus 300 is a fetus, it is critical for accurate diagnosis to determine a position of an organ of a fetus in the generated ultrasound image and an orientation in which the organ is formed. The position and orientation of an organ formed in the fetus are used as a basis for determining a direction in which the fetus is currently oriented and whether organs in the fetus are abnormally formed. By determining the position and orientation of an organ in the fetus, it is possible to diagnose the presence of physical abnormalities in the fetus before birth.

Position type information is information indicating types of positions where organs may be arranged in the fetus. The types of positions included in the position type information may be predetermined according to medical statistics. According to an embodiment, data related to the position type information may be stored in the storage (150 of FIG. 1) or be input via the input interface 310.

According to an embodiment, position type information may be situs solitus or situs abnormality. Situs abnormality may include one of situs inversus totalis, left isomerism, right isomerism, situs inversus thoracalis, and situs inversus abdominalis. The position type information will be described in more detail with reference to FIGS. 5A through 5F.

The position type information may be provided for the entire body of the fetus based on arrangement of organs throughout the entire body, or be provided for each part of the body based on arrangement of organs in some parts of the body. For example, the position type information may be provided as a plurality of pieces of information respectively including cardiac position information and abdominal organ position information or as a single piece of information into which the cardiac position information and the abdominal organ position information are integrated.

According to an embodiment, the cardiac position information may include one of levocardia, mesocardia, dextrocardia, and ectopiacordis. The cardiac position information will be described in more detail below with reference to FIG. 6.

According to an embodiment, the abdominal organ position information may include at least one of situs solitus and heterotaxia. The abdominal organ position information may include information about locations of lungs, liver, and spleen. The abdominal organ position information will be described in more detail below with reference to FIG. 7.

The interface for selecting position type information provides various pieces of predesignated position type information. Furthermore, the interface for selecting position type information may provide a selection window for selecting one or a plurality of pieces of position type information among the various pieces of predesignated position type information.

The processor 320 may control the input interface 310 to receive the selected position type information. According to an embodiment, the input interface 310 may be provided in the display 330. For example, a user may directly touch the interface for selecting position type information displayed on the display 330 to input the position type information.

The processor 320 may determine positions of organs in an ultrasound image, based on the input position type information. By respectively predicting orientations and positions of main organs based on the position type information, the processor 320 may more easily determine the positions of the organs. When a plurality of pieces of position type information are input, the processor 320 may determine positions of organs based on the plurality of pieces of position type information and select the positions of the organs with higher accuracy.

According to an embodiment, the processor 320 may determine left and right sides of a fetus based on the input position type information and the determined positions of the organs. Information about the left and right sides of the fetus represents orientations of left and right halves of the fetus. The left and right sides of the fetus may be determined based on determined positions and orientations of organs in the fetus. According to an embodiment, the left and right sides of the fetus may be determined by using a determined position and orientation of a blood vessel as main information. According to another embodiment, the left and right sides of the fetus may be determined by using a determined position and orientation of a cardiac axis as main information. A method of determining left and right sides of a fetus will be described in more detail below with reference to FIGS. 8A and 8B.

The processor 320 may respectively calculate pieces of information about organs based on input position type information and determined positions of the organs and control the display 330 to respectively display the calculated pieces of information together with an ultrasound image. According to an embodiment, information about each organ may include a name of the organ and a position and an orientation thereof in an ultrasound image. The processor 320 may control the display 330 to display a name of each organ at a position of the organ in an ultrasound image. Furthermore, the processor 320 may control the display 330 to display an orientation of each organ at a corresponding position in an ultrasound image in the form of an arrow. However, a method of displaying information about organs according to control by the processor 320 is not limited thereto. For example, the processor 320 may control the display 330 to display information about each organ by displaying a marker at a corresponding position in an ultrasound image or coloring the corresponding position.

In addition, the processor 320 may control the display 330 to display data associated with the input position type information, together with an ultrasound image. For example, the processor 320 may control the display 330 to display a name of the input position type information as a text, together with an ultrasound image. Alternatively, the processor 320 may control the display 330 to display an image obtained by rendering a schematic image of the input position type information, together with an ultrasound image.

Furthermore, the processor 320 may control the display 330 to display information about the determined left and right sides of the fetus together with an ultrasound image. For example, the processor 320 may control the display 330 to display information about the left and right sides of the fetus in the form of an arrow. However, a method of displaying information about the left and right sides of a fetus according to control by the processor 320 is not limited to the above-described example. For example, the processor 320 may control the display 330 to display information about each organ by applying different colors to an area where either the left or right half of the fetus is located in an ultrasound image, or by showing the information about the left and right sides of the fetus in the form of text.

The processor 320 may be formed as a hardware unit which includes a memory storing at least one of application data, an algorithm, and a program for controlling the display 330 to display information about each organ, which is calculated based on input position type information, together with an ultrasound image, and a processor for processing the application data, the algorithm, or the program stored in the memory. For example, the processor 320 may consist of a processor including at least one of a central processing unit (CPU), a microprocessor, and a graphics processing unit. In this case, the memory and the processor may be formed as a single chip, but are not limited thereto.

Figure 4:
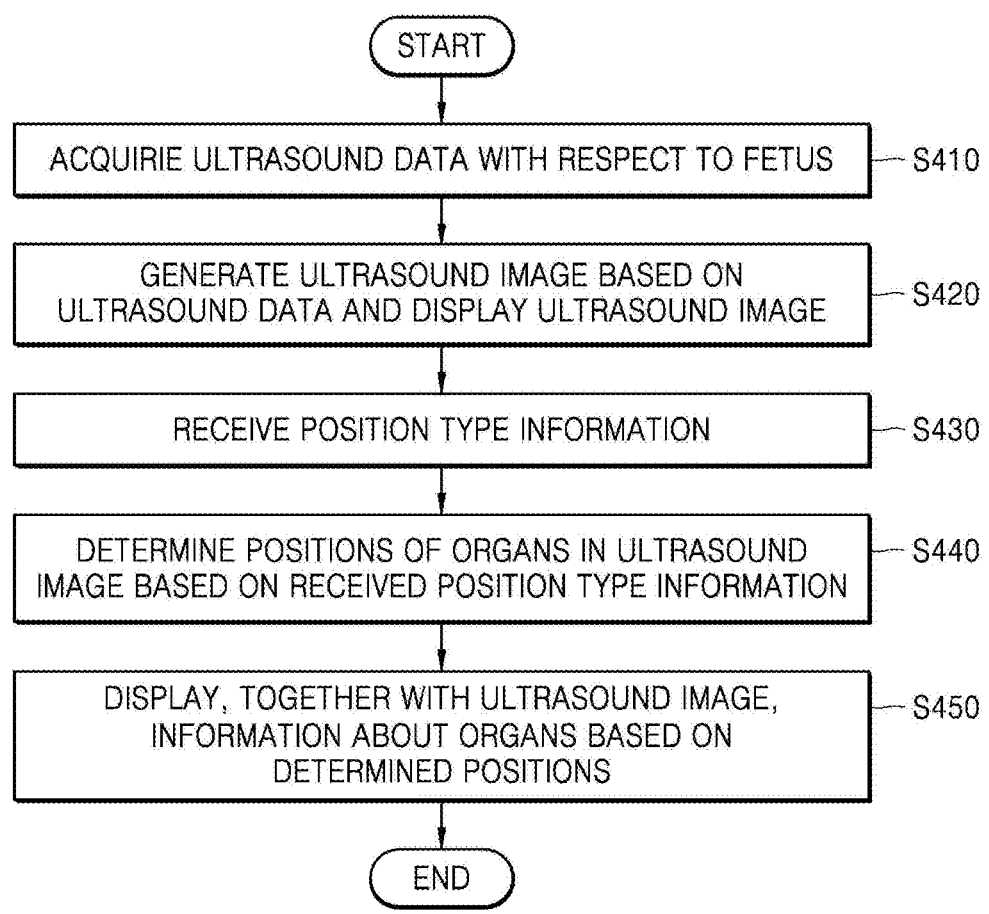
FIG. 4 is flowchart of a method of displaying an ultrasound image according to an embodiment.

FIG. 4 is flowchart of a method of displaying an ultrasound image according to an embodiment. The method of FIG. 4 is performed by an ultrasound diagnosis apparatus. The ultrasound diagnosis apparatus receives position type information from the outside and displays information about an organ, which is calculated based on the received position type information, together with an ultrasound image.

The ultrasound diagnosis apparatus acquires ultrasound data with respect to a fetus (S410). Detailed descriptions of the method, performed by the ultrasound diagnosis apparatus, of acquiring ultrasound data with respect to the fetus that is an object are already provided above with reference to FIG. 3.

The ultrasound diagnosis apparatus generates an ultrasound image based on the ultrasound data and displays the generated ultrasound image (S420). The ultrasound image may be displayed in various formats including at least one of an A mode, a B mode, and an M mode.

The ultrasound diagnosis apparatus receives position type information (S430). The position type information is information indicating types of positions where organs may be arranged in the fetus. The position type information may be provided for the entire body of the fetus based on arrangement of organs across the entire body, or be provided for each body part based on arrangement of organs in some parts of the body. For example, the position type information may be provided as a plurality of pieces of information respectively including cardiac position information and abdominal organ position information or as a single piece of information into which the cardiac position information and the abdominal organ position information are integrated.

According to an embodiment, the position type information may be situs solitus or situs abnormality. Situs abnormality may include one of situs inversus totalis, left isomerism, right isomerism, situs inversus thoracalis, and situs inversus abdominalis.

According to an embodiment, the cardiac position information may include one of levocardia, mesocardia, dextrocardia, and ectopiacordis. According to an embodiment, the abdominal organ position information may include at least one of situs solitus and heterotaxia. The abdominal organ position information may include information about locations of lungs, liver, and spleen.

The ultrasound diagnosis apparatus may display an interface for selecting position type information, via which a user inputs position type information. The interface for selecting position type information provides various pieces of predesignated position type information. According to an embodiment, the various pieces of predesignated position type information may be provided in a graphical form or as a text. Furthermore, according to an embodiment, the interface for selecting position type information may provide a selection window for selecting one or a plurality of pieces of position type information among the various pieces of predesignated position type information.

The ultrasound diagnosis apparatus may include an input interface for receiving a user input. The input interface may include hardware components such as a key pad, a mouse, a trackball, a touch pad, a touch screen, and a jog switch, but is not limited thereto. The ultrasound diagnosis apparatus may receive, via the input interface, selected position type information from the outside. A way in which the position type information is input may vary according to a configuration of the input interface. For example, the user may directly touch the interface for selecting position type information displayed on a display to input the position type information. According to an embodiment, the selection window may be implemented as an input form that allows the user to enter a name of position type information.

The ultrasound diagnosis apparatus determines positions of organs in an ultrasound image based on the received position type information (S440). By respectively predicting orientations and positions of main organs based on the received position type information, the ultrasound diagnosis apparatus may more easily determine the positions of the organs. When a plurality of pieces of position type information are input, the ultrasound diagnosis apparatus may determine positions of organs based on the plurality of pieces of position type information and select the positions of the organs with higher accuracy.

According to an embodiment, the processor 320 may determine left and right sides of a fetus based on the input position type information and the determined positions of the organs. Information about the left and right sides of the fetus represents orientations of left and right halves of the fetus. The left and right sides of the fetus may be determined based on determined positions and orientations of organs. According to an embodiment, the left and right sides of the fetus may be determined by using a determined position and orientation of a spine as main information. According to another embodiment, the left and right sides of the fetus may be determined by using a determined position and orientation of a cardiac axis as main information.

The ultrasound diagnosis apparatus displays, together with the ultrasound image, information about the organs based on the determined positions of the organs (S450). According to an embodiment, information about each organ may include a name of the organ and a position and an orientation thereof in the ultrasound image. The ultrasound diagnosis apparatus may display a name of each organ at a position of the organ in the ultrasound image, simultaneously with the ultrasound image. Furthermore, the ultrasound diagnosis apparatus may display an orientation of each organ at a corresponding position in the ultrasound image in the form of an arrow. However, a method, performed by the ultrasound diagnosis apparatus, of displaying information about organs is not limited thereto. For example, the ultrasound diagnosis apparatus may display information about each organ by displaying a marker at a corresponding position in the ultrasound image or coloring the corresponding position.

In addition, the ultrasound diagnosis apparatus may display data associated with the input position type information, together with the ultrasound image. For example, the ultrasound diagnosis apparatus may display a name of the input position type information as a text, together with the ultrasound image. Alternatively, the ultrasound diagnosis apparatus may display an image obtained by schematizing the input position type information, together with the ultrasound image.

Furthermore, the ultrasound diagnosis apparatus may display information about the determined left and right sides of the fetus together with the ultrasound image. For example, the ultrasound diagnosis apparatus may display the information about the left and right sides of the fetus in the form of an arrow at a lower end of the ultrasound image. However, a method, performed by the ultrasound diagnosis apparatus, of displaying information about the left and right sides of a fetus is not limited to the above-described example. For example, the ultrasound diagnosis apparatus may display information about each organ by applying different colors to an area where either the left or right half of the fetus is located in an ultrasound image, or by showing the information about the left and right sides of the fetus as a text.

FIGS. 5A through 5F are diagrams for explaining position type information according to an embodiment. Referring to FIGS. 5A through 5F, the position type information may be situs solitus or situs abnormality. Situs abnormality may include one of situs inversus totalis, left isomerism, right isomerism, situs inversus thoracalis, and situs inversus abdominalis. Although FIGS. 5A through 5F each show that information about the heart, lungs, liver, stomach, and spleen is included in position type information, this is merely an example, and types of organs included in the position type information are not limited thereto.

Situs solitus is a type of position in which all of the thoracic and abdominal organs are arranged at normal expected locations and correct orientations. On the other hand, situs abnormality is a type of position in which some or all of the thoracic or abdominal organs are arranged in abnormal locations or orientations.

Figure 5A:
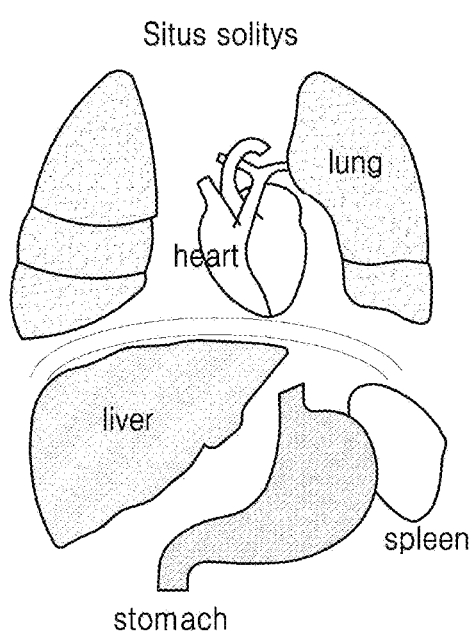
FIGS. 5A through 5F are diagrams for explaining position type information according to an embodiment.

FIG. 5A is a diagram for explaining position type information of a situs solitus. Since all organs are arranged at expected locations in the situs solitus, it may be determined that a fetus with the situs solitus is developing normally.

Figure 5B:
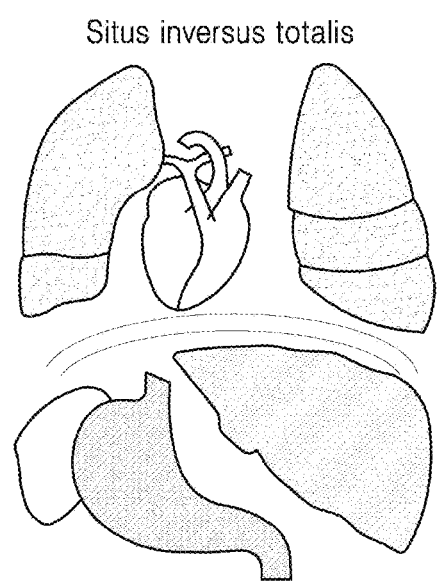

FIG. 5B is a diagram for explaining position type information of situs inversus totalis. Situs inversus totalis is a type of position characterized by anatomical arrangement of all organs in a mirror-image of situs solitus. The situs inversus totalis is a rare disease that is inherited in an autosomal recessive manner, and it may not greatly adversely affect daily life but may possibly cause various digestive diseases.

Figure 5C:
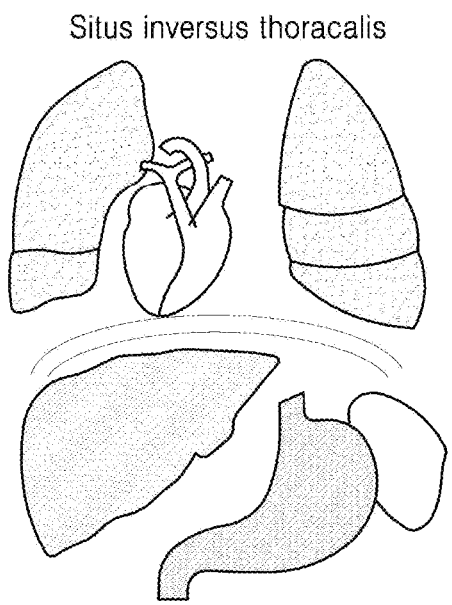
Figure 5D:
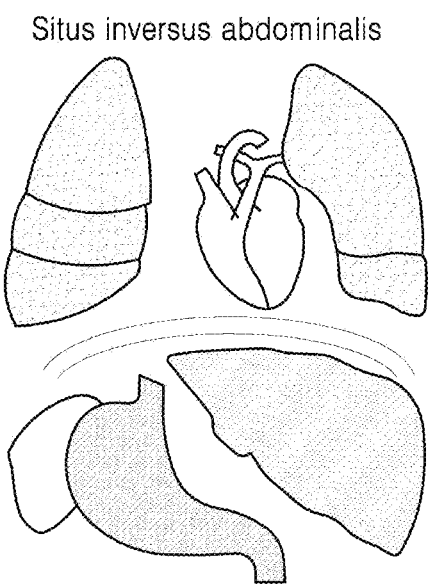

FIGS. 5C and 5D are diagrams for respectively explaining pieces of position type information that are situs inversus thoracalis and situs inversus abdominalis. Situs inversus thoracalis is a type of position in which arrangement of abdominal organs is normal whereas arrangement of thoracic organs is the mirror-image of situs solitus. On the other hand, situs inversus abdominalis is a type of position in which arrangement of thoracic organs is normal whereas arrangement of abdominal organs is the mirror image of situs solitus. Situs inversus including situs inversus thoracalis and situs inversus abdominalis is a type of position in which organs are arranged in a mirror-image of normal arrangement regardless of their functions. Thus, to avoid misdiagnosis and correctly diagnose a health condition of a fetus, it is important to determine in advance whether the inversion of position of organs occurs in the fetus.

Figure 5E:
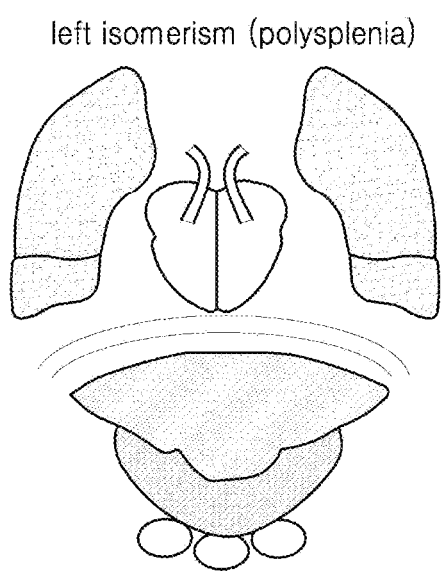
Figure 5F:
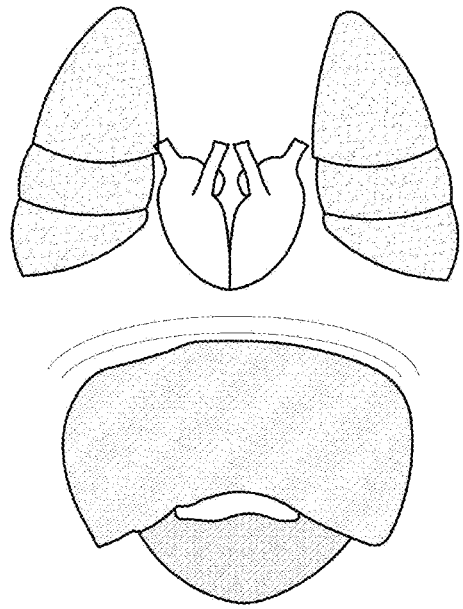

FIGS. 5E and 5F are diagrams for respectively explaining pieces of position type information that are left isomerism and right isomerism. Isomerism is a type of position characterized by arrangement in which organs on opposite sides of the body do not have a completely identical structure but are arranged in a symmetrical mirror image of each other. The left isomerism is a condition in which the right atrium is in a form of the left atrium having a small, narrow atrial appendage, while the right isomerism is a condition in which the left atrium is in a form of the right atrium having a broad atrial appendage.

According to an embodiment, an ultrasound diagnosis apparatus may receive current position type information of an object among pieces of predesignated position type information from the outside to more easily identify positions and orientations of organs in an ultrasound image and analyze information about the positions and orientations thereof. In addition, the ultrasound diagnosis apparatus may analyze the ultrasound image to autonomously select position type information that is most appropriate among stored pieces of position type information. In this case, the ultrasound diagnosis apparatus requires a large number of computations but may achieve more user convenience, compared to when receiving position type information from the outside.

Figure 6:
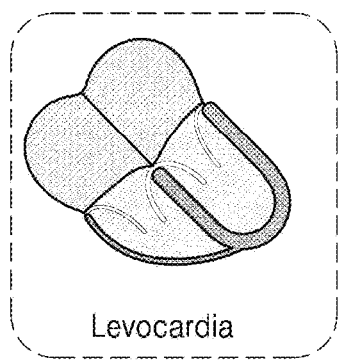
FIG. 6 is a diagram for explaining cardiac position information according to an embodiment.
Figure 6:
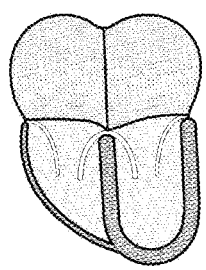
Figure 6:
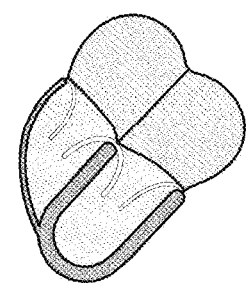

FIG. 6 is a diagram for explaining cardiac position information according to an embodiment. Referring to FIG. 6, the cardiac position information may include levocardia, mesocardia, or dextrocardia. However, this is merely an example, and types of the cardiac position information are not limited thereto. For example, the cardiac position information may further include ectopiacordis.

According to an embodiment, the cardiac position information is determined based on an orientation of a cardiac apex. Levocardia is a type of cardiac position in which the cardiac apex points to the left, and dextrocardia is a type of cardiac position in which the cardiac apex points to the right. Mesocardia is a type of cardiac position in which the cardiac apex points to a midline of the thorax. In general, when position type information of a fetus is situs solitus, the cardiac apex points to the left, so the cardiac position information of the fetus is levocardia. On the other hand, a fetus with situs inversus totalis has a dextrocardia since the cardiac apex points to the right.

Figure 7:
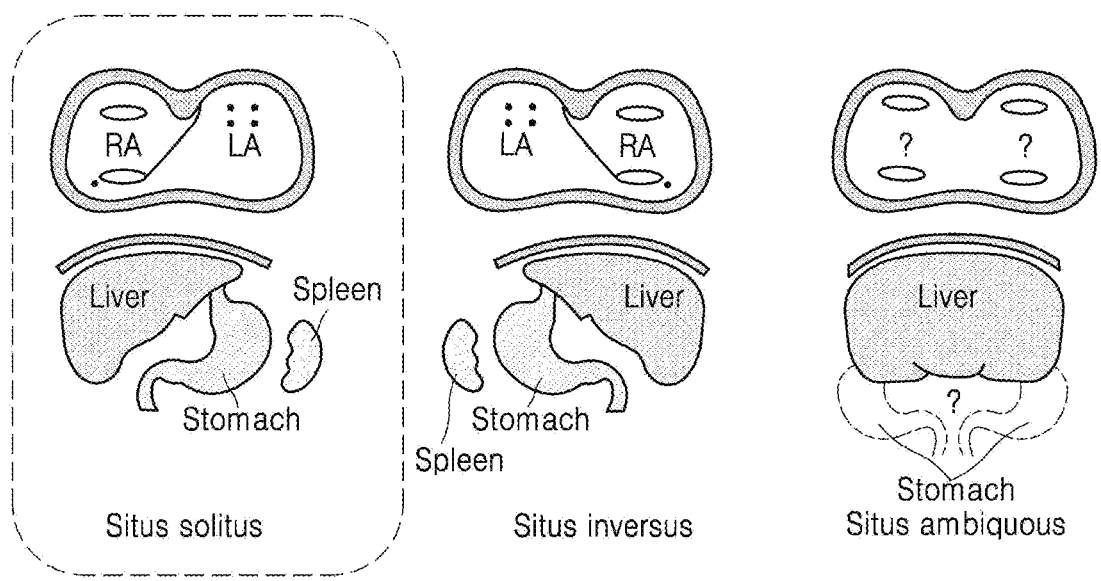
FIG. 7 is a diagram for explaining abdominal organ position information according to an embodiment.

FIG. 7 is a diagram for explaining abdominal organ position (visceral situs) information according to an embodiment. Referring to FIG. 7, the abdominal organ position information may include one of situs solitus, situs inversus, and situs ambiguous. However, this is merely an example, and types of the abdominal organ position information are not limited thereto. Furthermore, although FIG. 7 shows that information about the liver, stomach, and spleen is included in the abdominal organ position information, this is merely an example, and types of organs included in the abdominal organ position information are not limited thereto.

Situs solitus is a type of position in which all of the abdominal organs are correctly arranged at expected locations. On the other hand, situs inversus is a type of position characterized by an anatomical arrangement of the abdominal organs in a mirror-image of situs solitus. Situs ambiguous is a type of position characterized by indeterminate arrangement of organs, e. g., a condition in which some organs are not centered correctly, are each divided into several portions, or are absent altogether.

Figure 8A:
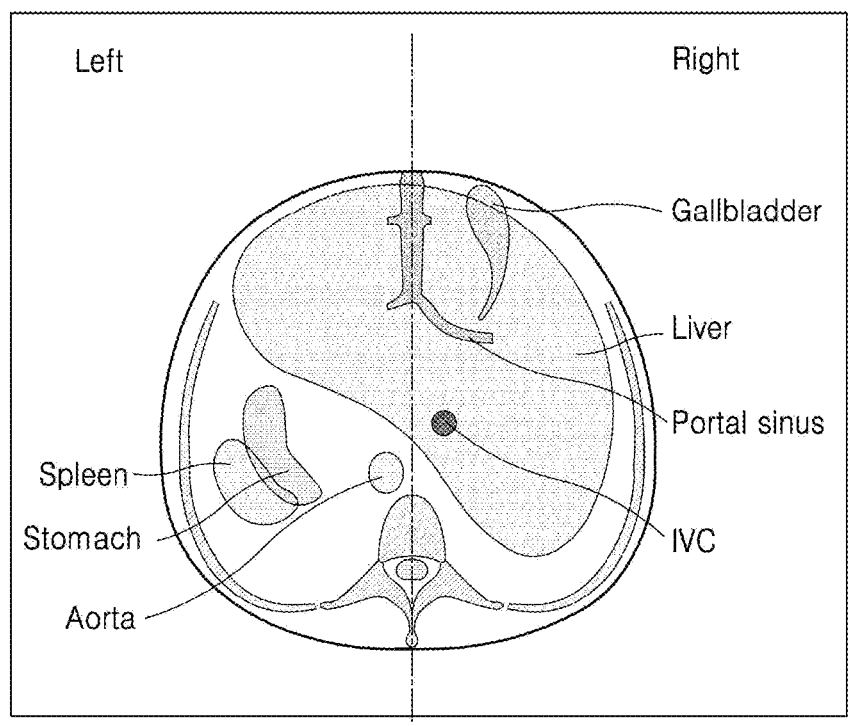
FIGS. 8A and 8B are diagrams for explaining methods of determining left and right sides of a fetus, according to embodiments.
Figure 8B:
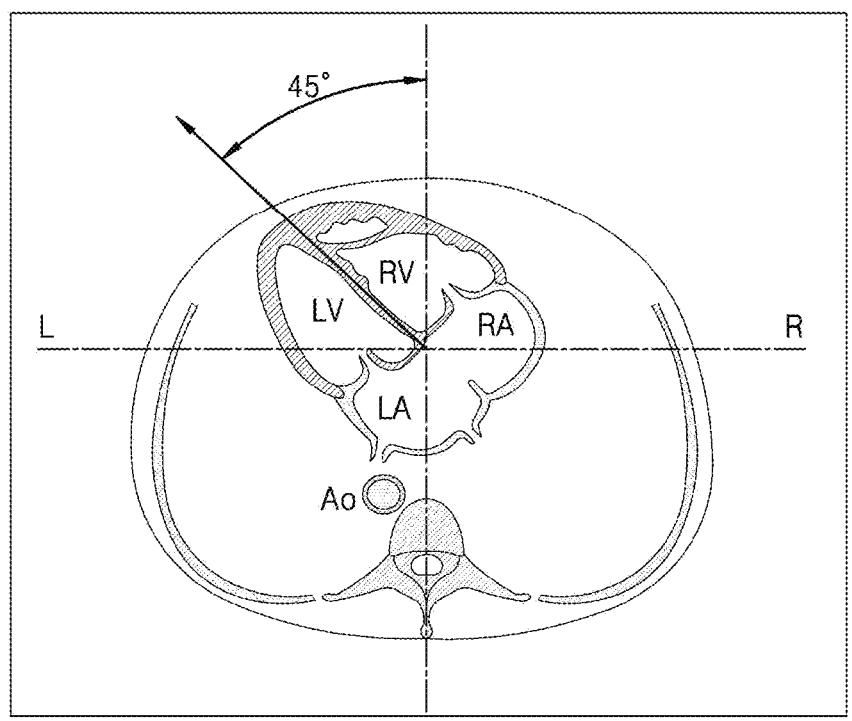

FIGS. 8A and 8B are diagrams for explaining methods of determining left and right sides of a fetus, according to embodiments. Information about the left and right sides of the fetus represents orientations of left and right halves of the fetus. The left and right sides of the fetus may be determined based on determined positions and orientations of organs in the fetus.

Referring to FIG. 8A, according to an embodiment, the left and right sides of the fetus may be determined by using determined positions and orientations of blood vessels as main information. FIG. 8A illustrates a method of determining the left and right sides of the fetus in an abdominal view ultrasound image according to an embodiment. In the abdominal view ultrasound image, positions of an aorta, an inferior vena cava (IVC), and a portal sinus may be identified, together with positions of other abdominal organs including the liver, spleen, stomach, gallbladder, etc. The ultrasound diagnosis apparatus may determine the left and right sides of the fetus based on the identified positions of the organs and input position type information and display information about the left and right sides of the fetus defined with respect to a central axis.

Referring to FIG. 8B, according to another embodiment, the left and right sides of the fetus may be determined by using a determined position and orientation of a cardiac axis as main information. FIG. 8B illustrates a method of determining the left and right sides of a fetus in a 4-chamber view ultrasound image according to an embodiment. Positions of four chambers of the heart including left and right atria LA and RA and left and right ventricles LV and RV and an aorta Ao may be identified in the 4-chamber view ultrasound image. The ultrasound diagnosis apparatus may determine a cardiac axis and a cardiac apex based on the positions of the four chambers of the heart. The ultrasound diagnosis apparatus may also determine the left and right sides of the fetus based on the determined cardiac axis and cardiac apex and display information about the left and right sides of the fetus defined with respect to a central axis.

FIGS. 9A through 9E are diagrams for explaining methods of displaying organ information in an ultrasound image, according to embodiments.

Figure 9A:
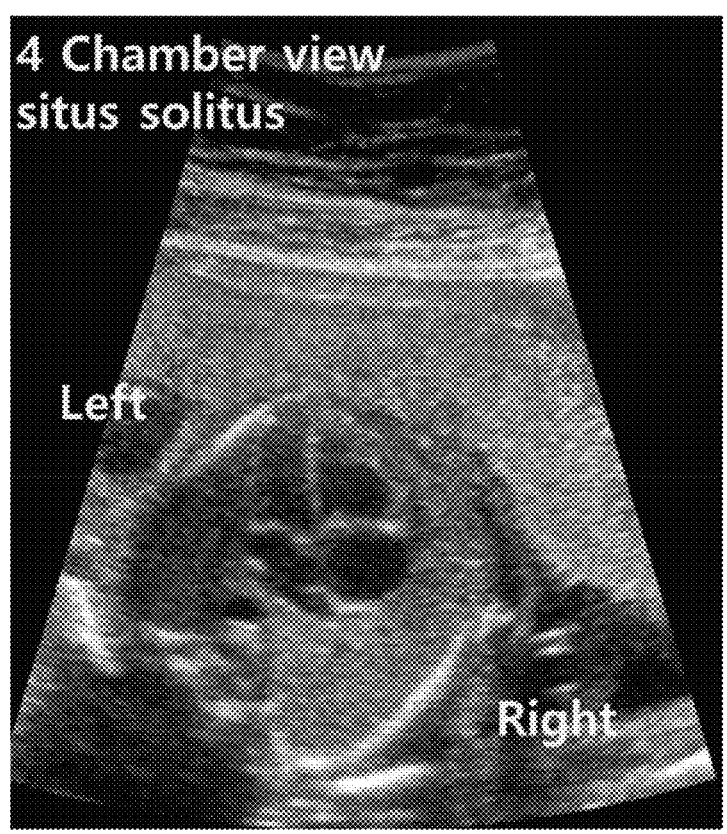
FIGS. 9A through 9E are diagrams for explaining methods of displaying organ information in an ultrasound image, according to an embodiment.

FIG. 9A illustrates an example in which a name of selected position information and information about the left and right sides of a fetus are displayed together with a 4-chamber view ultrasound image, according to an embodiment. Referring to FIG. 9A, a name of situs solitus that is selected position type information is displayed as a text at an upper left end of the 4-chamber view ultrasound image, and the information about the left and right sides of the fetus is shown as a text according to determined orientations. However, this is merely an example, and a method of displaying organ information according to an embodiment is not limited thereto.

Figure 9B:

FIG. 9B illustrates an example in which a name of selected position information and information about the left and right sides of a fetus are displayed together with a 4-chamber view ultrasound image, according to an embodiment. Referring to FIG. 9B, a name of situs solitus that is selected position type information is displayed in the form of a text at an upper left end of the 4-chamber view ultrasound image, and the information about the left and right sides of the fetus is indicated by arrow axes according to determined orientations. However, this is merely an example, and a method of displaying organ information according to an embodiment is not limited thereto.

Figure 9C:
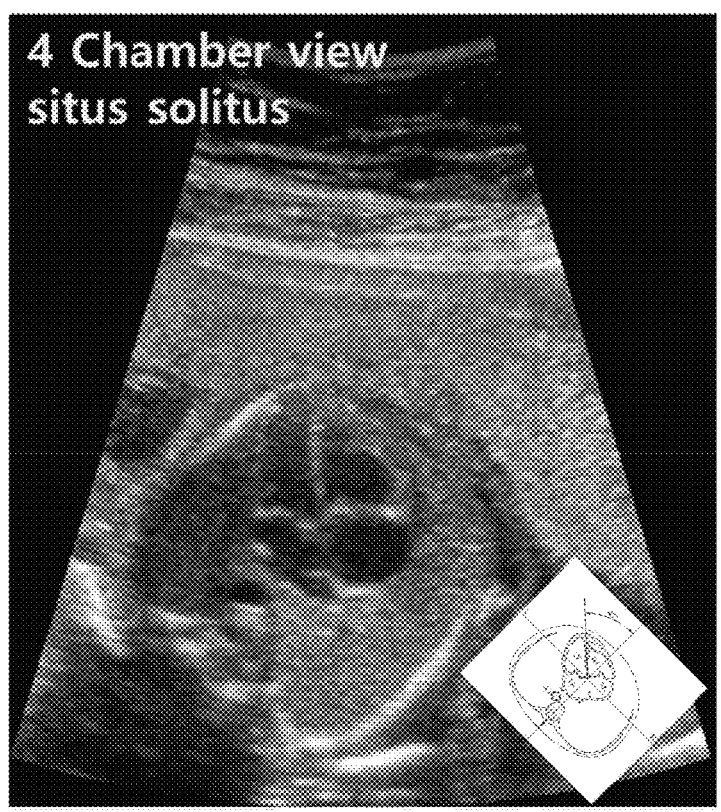

FIG. 9C illustrates an example in which a name of selected position information and information about the left and right sides of a fetus are displayed together with a 4-chamber view ultrasound image, according to an embodiment. Referring to FIG. 9C, a name of situs solitus that is one from among pieces of selected position type information is displayed as a text at an upper left end of the 4-chamber view ultrasound image. Furthermore, cardiac position information that is another piece of selected position type information is displayed as a graphic image, together with the information about the left and right sides of the fetus, at a lower right end of the 4-chamber view ultrasound image. In this case, the cardiac position information is selected because the 4-chamber view ultrasound image is used. When an abdominal view ultrasound image is used instead, abdominal organ position information may be displayed as position type information. However, this is merely an example, and a method of displaying organ information according to an embodiment is not limited thereto.

Figure 9D:

FIG. 9D illustrates an example in which determined positions of organs may be displayed together with a 4-chamber view ultrasound image, according to an embodiment. Referring to FIG. 9D, positions and orientations of atria and ventricles of the heart are respectively determined, and information about the determined positions is displayed by applying different colors to their corresponding positions in the 4-chamber view ultrasound image. However, this is merely an example, and a method of displaying organ information according to an embodiment is not limited thereto.

Figure 9E:
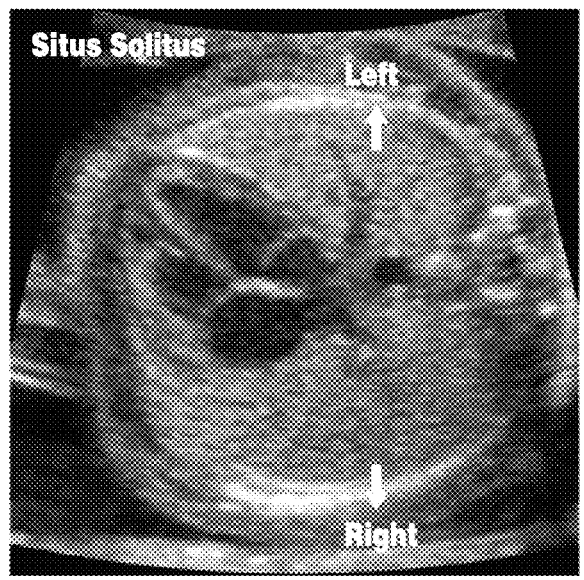

FIG. 9E illustrates an example in which a name of selected position information and information about the left and right sides of a fetus are displayed together with a 4-chamber view ultrasound image, according to an embodiment. Referring to FIG. 9E, a name of situs solitus that is one from among pieces of selected position type information is displayed as a text at an upper left end of the 4-chamber view ultrasound image, and the information about the left and right sides of the fetus is indicated by arrows according to determined orientations. However, this is merely an example, and a method of displaying organ information according to an embodiment is not limited thereto.

Embodiments may be implemented through non-transitory computer-readable recording media having recorded thereon computer-executable instructions and data. The instructions may be stored in the form of program codes, and when executed by a processor, generate a predetermined program module to perform a specific operation. Furthermore, when being executed by the processor, the instructions may perform specific operations according to the embodiments.

What is claimed is:

1. An ultrasound diagnosis apparatus comprising:
a storage configured to store data related to first position type information;
a probe configured to transmit an ultrasound signal to an object including a fetus, and receive an ultrasound echo signal reflected from the object;
one or more processors configured to acquire ultrasound image data with respect to the fetus based on the ultrasound echo signal and generate an ultrasound image based on the ultrasound image data; and
a display configured to display the ultrasound image, wherein the first position type information and second position type information are information which are predetermined according to medical statistics, wherein the first position time information indicates position information of a heart, which is one position selected from left isomerism (polysplenia) and right isomerism (asplenia), wherein the second position type information indicates position information of an abdomen, which is one position selected from among situs solitus, situs inversus totalis, situs inversus thoracalis, and situs inversus abdominalis, wherein the one or more processors are further configured to detect one from among the first position type information and the second position type information that is predetermined and corresponds to the ultrasound image, obtain third position type information related to one of the heart and the abdomen from the one from among the first position type information and the second position type information, and control the display to display the third position type information related to the heart or the abdomen together with the ultrasound image, based on the one from among the first position type information and the second position type information, and wherein the one or more processors autonomously select one from among the first position type information and the second position type information that are stored and control the display to display selected position type information with the third position type information.

2. The ultrasound diagnosis apparatus of claim 1, wherein the storage is further configured to store data related to one position among levocardia, mesocardia, dextrocardia, and ectopiacordis as the first position type information.

3. The ultrasound diagnosis apparatus of claim 1, wherein the one or more processors are further configured to control, based on the one from among the first position type information and the second position type information, the display to display one from among a name and an orientation of each of the organs at their corresponding positions, together with the ultrasound image.

4. The ultrasound diagnosis apparatus of claim 1, wherein the one or more processors are further configured to:
determine a left side and a right side of the fetus, based on the one from among the first position type information and the second position type information; and
control the display to display information related to the determined left side and the determined right side of the fetus together with the ultrasound image.

5. The ultrasound diagnosis apparatus of claim 4, wherein the one or more processors are further configured to control the display to display, together with the ultrasound image, the information related to the left side and the right side of the fetus in a form of an arrow.

6. The ultrasound diagnosis apparatus of claim 1, wherein the one or more processors are further configured to control the display to display the one from among the first position type information and the second position type information together with the ultrasound image.

7. A method of displaying an ultrasound image by using an ultrasound diagnosis apparatus including a storage, an input interface, a probe, a processor, and a display, the method comprising:
storing, by the storage, data related to first position type information and second position type information;
transmitting, by the probe, an ultrasound signal to an object including a fetus;
receiving, by the probe, an ultrasound echo signal reflected from the object;
acquiring, by the processor, ultrasound image data with respect to the fetus based on the ultrasound echo signal;
generating, by the processor, the ultrasound image based on the ultrasound image data and displaying, by the display, the ultrasound image;
detecting, by the processor, one from among the first position type information and the second position type information that is predetermined and corresponds to the ultrasound image;
obtaining, by the processor, third position type information related to organs from the one from among the first position type information and the second position type information; and
displaying, by the display, the third position type information related to the organs together with the ultrasound image, based on the one from among the first position type information and the second position type information, wherein the first position type information and the second position type information are information which are predetermined according to medical statistics, wherein the first position time information indicates position information of a heart, which is one position selected from left isomerism (polysplenia) and right isomerism (asplenia), wherein the second position type information indicates position information of an abdomen, which is one position selected from among situs solitus, situs inversus totalis, situs inversus thoracalis, and situs inversus abdominalis, wherein the processor autonomously selects one from among the first position type information and the second position type information that are stored and controls the display to display selected position type information with the third position type information.

8. The method of claim 7,
wherein the storing the data related to the first position type information comprises receiving a cardiac position.

9. The method of claim 7, wherein the displaying of the third position type information related to the organs together with the ultrasound image based on the one from among the first position type information and the second position type information comprises displaying one from among a name and an orientation of each of the organs at their corresponding positions, together with the ultrasound image.

10. The method of claim 7, further comprising:
determining a left side and a right side of the fetus, based on the one from among the first position type information and the second position type information; and
displaying information related to the determined left side and the determined right side of the fetus together with the ultrasound image.

11. The method of claim 10, wherein the displaying of the information related to the determined left side and the determined right side of the fetus comprises displaying, together with the ultrasound image, the information related to the determined left side and the determined right side of the fetus as a text.

12. A non-transitory computer-readable recording medium having stored therein a computer program code which, when read and executed by a processor included in an ultrasound diagnosis apparatus further including a storage, an input interface, a probe, and a display, performs a method of displaying an ultrasound image, the method comprising:

storing, by the storage, data related to first position type information;

transmitting, by the probe, an ultrasound signal to an object including a fetus;

receiving, by the probe, an ultrasound echo signal reflected from the object;

acquiring, by the processor, ultrasound image data with respect to the fetus based on the ultrasound echo signal;

generating, by the processor, the ultrasound image based on the ultrasound image data and displaying the ultrasound image;

detecting, by the processor, one from among the first position type information and second position type information that is predetermined and corresponds to the ultrasound image;

obtaining, by the processor, third position type information related to organs from the one from among the first position type information and the second position type information; and displaying, by the display, the third position type information related to the organs together with the ultrasound image, based on the one from among the first position type information and the second position type information, wherein the first position type information and the second position type information are information which are predetermined according to medical statistics, wherein the first position time information indicates position information of a heart, which is one position selected from left isomerism (polysplenia) and right isomerism (asplenia), wherein the second position type information indicates position information of an abdomen, which is one position selected from among situs solitus, situs inversus totalis, situs inversus thoracalis, and situs inversus abdominalis, wherein the processor autonomously selects one from among the first position type information and the second position type information that are stored and controls the display to display selected position type information with the third position type information.

* * * * *